(12) United States Patent
Salahieh

(10) Patent No.: US 12,201,521 B2
(45) Date of Patent: Jan. 21, 2025

(54) ANCHOR POSITION VERIFICATION FOR PROSTHETIC CARDIAC VALVE DEVICES

(71) Applicant: Shifamed Holdings, LLC, Campbell, CA (US)

(72) Inventor: Amr Salahieh, Saratoga, CA (US)

(73) Assignee: Shifamed Holdings, LLC, Campbell, CA (US)

(*) Notice: Subject to any disclaimer, the term of this patent is extended or adjusted under 35 U.S.C. 154(b) by 201 days.

(21) Appl. No.: 17/655,978

(22) Filed: Mar. 22, 2022

(65) Prior Publication Data

US 2023/0044256 A1    Feb. 9, 2023

Related U.S. Application Data

(60) Provisional application No. 63/164,514, filed on Mar. 22, 2021.

(51) Int. Cl.
*A61F 2/24* (2006.01)
*A61M 5/00* (2006.01)

(52) U.S. Cl.
CPC ........... *A61F 2/2418* (2013.01); *A61M 5/007* (2013.01); *A61F 2220/0008* (2013.01); *A61F 2250/0098* (2013.01); *A61M 2210/125* (2013.01)

(58) Field of Classification Search
CPC .... A61F 2/2409; A61F 2/2412; A61F 2/2418; A61F 2/2463; A61F 2230/0091; A61F 2/07; A61F 2/95; A61F 2/958; A61F 2/82; A61F 2/90; A61F 2/915; A61F 2/91; A61F 2250/0067; A61F 2/2466; A61F 2/2427; A61F 2/04; A61F 2002/075; A61F 2/06; A61F 2220/0008; A61F 2/89; A61F 2/954; A61F 2/24; A61F 2/246; A61F 2/01; A61F 2250/0069; A61F 2/2442; A61F 2/2457; A61F 2002/823; A61F 2002/821;
(Continued)

(56) References Cited

U.S. PATENT DOCUMENTS

| 4,725,274 A | 2/1988 | Lane et al. |
| 5,002,563 A | 3/1991 | Pyka et al. |
| 5,327,905 A | 7/1994 | Avitall |

(Continued)

FOREIGN PATENT DOCUMENTS

| AU | 2012261727 B2 | 10/2015 |
| AU | 2019246822 B2 | 8/2020 |

(Continued)

OTHER PUBLICATIONS

Saul; U.S. Appl. No. 17/773,193 entitled "Prosthetic cardiac valve delivery devices, systems, and methods," filed Apr. 29, 2022.

(Continued)

*Primary Examiner* — Seema Mathew
(74) *Attorney, Agent, or Firm* — Shay Glenn LLP

(57) ABSTRACT

A device for treating a diseased native valve in a patient is provided, the device including a frame structure and a plurality of leaflets. The device can further include a spiral anchor configured to extend around an outer circumference of the frame structure. The anchor can be configured to deliver a contrast agent into or near a target tissue. Other embodiments and methods of use are also provided.

17 Claims, 9 Drawing Sheets

(58) Field of Classification Search
CPC .......... A61F 2/94; A61F 2/2445; A61F 2/241;
A61F 2/242; A61F 2002/077; A61F
2250/0063
See application file for complete search history.

(56) References Cited

U.S. PATENT DOCUMENTS

| | | | |
|---|---|---|---|
| 5,356,424 A | 10/1994 | Buzerak et al. | |
| 5,370,685 A | 12/1994 | Stevens | |
| 5,582,616 A | 12/1996 | Bolduc et al. | |
| 5,716,397 A * | 2/1998 | Myers | A61F 2/2445 606/1 |
| 5,755,601 A | 5/1998 | Jones | |
| 5,779,669 A | 7/1998 | Haissaguerre et al. | |
| 5,873,835 A | 2/1999 | Hastings et al. | |
| 5,944,690 A | 8/1999 | Falwell et al. | |
| 5,997,526 A | 12/1999 | Giba et al. | |
| 6,048,339 A | 4/2000 | Zirps et al. | |
| 6,053,873 A | 4/2000 | Govari et al. | |
| 6,254,550 B1 | 7/2001 | McNamara et al. | |
| 6,419,695 B1 | 7/2002 | Gabbay | |
| 6,419,696 B1 * | 7/2002 | Ortiz | A61F 2/2409 623/2.37 |
| 6,530,952 B2 | 3/2003 | Vesely | |
| 6,533,783 B1 | 3/2003 | Töllner | |
| 6,641,553 B1 | 11/2003 | Chee et al. | |
| 6,752,813 B2 | 6/2004 | Goldfarb et al. | |
| 6,908,478 B2 | 6/2005 | Alferess et al. | |
| 6,964,684 B2 | 11/2005 | Ortiz et al. | |
| 6,974,476 B2 | 12/2005 | McGuckin, Jr. et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,160,322 B2 | 1/2007 | Gabbay | |
| 7,175,656 B2 | 2/2007 | Khairkhahan | |
| 7,201,771 B2 | 4/2007 | Lane | |
| 7,226,467 B2 | 6/2007 | Lucatero et al. | |
| 7,381,219 B2 | 1/2008 | Salahieh et al. | |
| 7,329,279 B2 | 2/2008 | Haug et al. | |
| 7,445,631 B2 | 11/2008 | Salahieh et al. | |
| 7,470,285 B2 | 12/2008 | Nugent et al. | |
| 7,527,647 B2 | 5/2009 | Spence | |
| 7,534,261 B2 | 5/2009 | Freidman | |
| 7,563,267 B2 | 7/2009 | Goldfarb et al. | |
| 7,594,903 B2 | 9/2009 | Webler et al. | |
| 7,604,646 B2 | 10/2009 | Goldfarb et al. | |
| 7,608,091 B2 | 10/2009 | Goldfarb et al. | |
| 7,618,449 B2 | 11/2009 | Tremulis et al. | |
| 7,621,948 B2 | 11/2009 | Herrmann et al. | |
| 7,666,204 B2 | 2/2010 | Thornton et al. | |
| 7,704,269 B2 | 4/2010 | St. Goar et al. | |
| 7,731,705 B2 | 6/2010 | Wardle | |
| 7,748,389 B2 | 7/2010 | Salahich et al. | |
| 7,749,266 B2 | 7/2010 | Forster et al. | |
| 7,780,725 B2 | 8/2010 | Haug et al. | |
| 7,799,069 B2 | 9/2010 | Bailey et al. | |
| 7,811,296 B2 | 10/2010 | Goldfarb et al. | |
| 7,824,442 B2 | 11/2010 | Salahieh et al. | |
| 7,824,443 B2 | 11/2010 | Salahieh et al. | |
| 7,846,203 B2 | 12/2010 | Cribier | |
| 7,942,927 B2 * | 5/2011 | Kaye | A61F 2/2445 623/2.11 |
| 7,947,075 B2 | 5/2011 | Goetz et al. | |
| 7,951,195 B2 | 5/2011 | Antonsson et al. | |
| 7,959,666 B2 | 6/2011 | Salahieh et al. | |
| 7,988,724 B2 | 8/2011 | Salahleh et al. | |
| 8,021,421 B2 | 9/2011 | Fogarty et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,070,800 B2 | 12/2011 | Lock et al. | |
| 8,075,615 B2 | 12/2011 | Eberhardt et al. | |
| 8,096,985 B2 | 1/2012 | Legaspi et al. | |
| 8,147,541 B2 | 4/2012 | Forster et al. | |
| 8,147,542 B2 | 4/2012 | Maisano et al. | |
| 8,182,528 B2 | 5/2012 | Salahleh et al. | |
| 8,216,256 B2 | 7/2012 | Raschdorf et al. | |
| 8,236,049 B2 | 8/2012 | Rowe et al. | |
| 8,241,351 B2 | 8/2012 | Cabiri | |
| 8,251,977 B2 | 8/2012 | Partlett | |
| 8,252,050 B2 | 8/2012 | Maisano et al. | |
| 8,287,584 B2 | 10/2012 | Salahleh et al. | |
| 8,313,526 B2 | 11/2012 | Hoffman et al. | |
| 8,323,241 B2 | 12/2012 | Salahich et al. | |
| 8,323,336 B2 | 12/2012 | Hill et al. | |
| 8,328,868 B2 | 12/2012 | Paul et al. | |
| 8,343,213 B2 | 1/2013 | Salahleh et al. | |
| 8,348,995 B2 | 1/2013 | Tuval et al. | |
| 8,348,996 B2 | 1/2013 | Tuval et al. | |
| 8,366,767 B2 | 2/2013 | Zhang | |
| 8,403,981 B2 | 3/2013 | Forster et al. | |
| 8,403,983 B2 | 3/2013 | Quadri et al. | |
| 8,414,643 B2 | 4/2013 | Tuval et al. | |
| 8,414,644 B2 | 4/2013 | Quadri et al. | |
| 8,414,645 B2 | 4/2013 | Dwork et al. | |
| 8,425,593 B2 | 4/2013 | Braido et al. | |
| 8,449,599 B2 | 5/2013 | Chau et al. | |
| 8,454,686 B2 | 6/2013 | Alkhatib | |
| 8,465,541 B2 | 6/2013 | Dwork | |
| 8,500,800 B2 | 8/2013 | Maisano et al. | |
| 8,512,401 B2 | 8/2013 | Murray et al. | |
| 8,523,881 B2 | 9/2013 | Cabiri et al. | |
| 8,545,553 B2 | 10/2013 | Zipory et al. | |
| 8,556,963 B2 | 10/2013 | Tremulis et al. | |
| 8,562,645 B2 | 10/2013 | Stone et al. | |
| 8,562,673 B2 | 10/2013 | Yeung et al. | |
| 8,579,962 B2 | 11/2013 | Salahleh et al. | |
| 8,603,157 B2 | 12/2013 | Seguin et al. | |
| 8,603,160 B2 | 12/2013 | Salahieh et al. | |
| 8,623,075 B2 | 1/2014 | Murray et al. | |
| 8,628,570 B2 | 1/2014 | Seguin | |
| 8,641,727 B2 | 2/2014 | Starksen et al. | |
| 8,652,202 B2 | 2/2014 | Alon et al. | |
| 8,652,203 B2 | 2/2014 | Quadri et al. | |
| 8,657,872 B2 | 2/2014 | Seguin | |
| 8,663,322 B2 * | 3/2014 | Keranen | A61F 2/2448 623/2.37 |
| 8,685,086 B2 | 4/2014 | Navia et al. | |
| 8,696,693 B2 | 4/2014 | Najafi et al. | |
| 8,715,342 B2 | 5/2014 | Zipory et al. | |
| 8,740,976 B2 | 6/2014 | Tran et al. | |
| 8,784,479 B2 | 7/2014 | Antonsson et al. | |
| 8,790,367 B2 | 7/2014 | Nguyen et al. | |
| 8,808,368 B2 | 8/2014 | Maisano et al. | |
| 8,828,078 B2 | 9/2014 | Salahieh et al. | |
| 8,834,564 B2 | 9/2014 | Tuval et al. | |
| 8,840,663 B2 | 9/2014 | Salahieh et al. | |
| 8,840,664 B2 | 9/2014 | Karapetian et al. | |
| 8,845,588 B2 | 9/2014 | Bruszewski | |
| 8,852,271 B2 | 10/2014 | Murray et al. | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,900,294 B2 | 12/2014 | Paniagua et al. | |
| 8,911,494 B2 | 12/2014 | Hammer et al. | |
| 8,920,369 B2 | 12/2014 | Salahieh et al. | |
| 8,926,690 B2 | 1/2015 | Kowalsky | |
| 8,926,696 B2 | 1/2015 | Cabiri et al. | |
| 8,926,697 B2 | 1/2015 | Gross et al. | |
| 8,940,002 B2 | 1/2015 | Goertzen | |
| 8,940,044 B2 | 1/2015 | Hammer et al. | |
| 8,951,299 B2 | 2/2015 | Paul et al. | |
| 8,986,371 B2 | 3/2015 | Quill et al. | |
| 8,998,980 B2 | 4/2015 | Shipley et al. | |
| 9,005,273 B2 | 4/2015 | Salahleh et al. | |
| 9,011,515 B2 | 4/2015 | Schweich et al. | |
| 9,011,523 B2 | 4/2015 | Seguin | |
| 9,011,530 B2 | 4/2015 | Reich et al. | |
| 9,017,408 B2 | 4/2015 | Siegal et al. | |
| 9,023,100 B2 | 5/2015 | Quadri et al. | |
| 9,034,032 B2 | 5/2015 | McLean et al. | |
| 9,039,757 B2 | 5/2015 | McLean et al. | |
| 9,056,009 B2 | 6/2015 | Keränen | |
| 9,061,120 B2 | 6/2015 | Osypka et al. | |

(56) References Cited

U.S. PATENT DOCUMENTS

| | | |
|---|---|---|
| 9,095,431 B2 | 8/2015 | Yu et al. |
| 9,119,719 B2 | 9/2015 | Zipory et al. |
| 9,125,739 B2 | 9/2015 | Paniagua et al. |
| 9,125,740 B2 | 9/2015 | Morriss et al. |
| 9,155,619 B2 | 10/2015 | Liu et al. |
| 9,168,129 B2 | 10/2015 | Valdez et al. |
| 9,168,131 B2 | 10/2015 | Yohanan et al. |
| 9,173,713 B2 | 11/2015 | Hart et al. |
| 9,173,737 B2 | 11/2015 | Hill et al. |
| 9,180,006 B2 | 11/2015 | Keränen |
| 9,226,823 B2 | 1/2016 | Dwork |
| 9,232,995 B2 | 1/2016 | Kovalsky et al. |
| 9,277,994 B2 | 3/2016 | Miller et al. |
| 9,289,297 B2 * | 3/2016 | Wilson .............. A61F 2/2466 |
| 9,295,547 B2 | 3/2016 | Costello et al. |
| 9,301,756 B2 | 4/2016 | Wardle |
| 9,301,836 B2 | 4/2016 | Buchbinder et al. |
| 9,320,597 B2 | 4/2016 | Savage et al. |
| 9,343,224 B2 | 5/2016 | Zilbershlag |
| 9,358,110 B2 | 6/2016 | Paul et al. |
| 9,414,915 B2 | 8/2016 | Lombardi et al. |
| 9,427,315 B2 | 8/2016 | Schweich et al. |
| 9,439,757 B2 | 9/2016 | Wallace et al. |
| 9,468,525 B2 | 10/2016 | Kovalsky |
| 9,474,606 B2 * | 10/2016 | Zipory .............. A61F 2/2457 |
| 9,474,840 B2 | 10/2016 | Siess |
| 9,480,559 B2 | 11/2016 | Vidlund et al. |
| 9,492,273 B2 | 11/2016 | Wallace et al. |
| 9,526,487 B2 | 12/2016 | Rahmani |
| 9,526,609 B2 | 12/2016 | Salahieh et al. |
| 9,532,868 B2 | 1/2017 | Braido |
| 9,532,870 B2 | 1/2017 | Cooper et al. |
| 9,561,102 B2 | 2/2017 | Rust et al. |
| 9,579,198 B2 | 2/2017 | Deem et al. |
| 9,636,224 B2 | 5/2017 | Zipory et al. |
| 9,636,481 B2 | 5/2017 | Campbell et al. |
| 9,662,202 B2 | 5/2017 | Quill et al. |
| 9,662,206 B2 | 5/2017 | Börtlein et al. |
| 9,662,209 B2 | 5/2017 | Gross et al. |
| 9,675,454 B2 | 6/2017 | Vidlund et al. |
| 9,681,952 B2 | 6/2017 | Hacohen et al. |
| 9,687,343 B2 | 6/2017 | Börtlein et al. |
| 9,724,192 B2 | 8/2017 | Sheps et al. |
| 9,730,790 B2 | 8/2017 | Quadri et al. |
| 9,730,793 B2 | 8/2017 | Reich et al. |
| 9,744,031 B2 | 8/2017 | Girard et al. |
| 9,744,038 B2 | 8/2017 | Dahlgren et al. |
| 9,750,605 B2 | 9/2017 | Ganesan et al. |
| 9,763,779 B2 | 9/2017 | Börtlein et al. |
| 9,763,780 B2 | 9/2017 | Morriss et al. |
| 9,814,611 B2 | 11/2017 | Cartledge et al. |
| 9,827,090 B2 | 11/2017 | Hill et al. |
| 9,861,480 B2 | 1/2018 | Zakai et al. |
| 9,867,700 B2 | 1/2018 | Bakis et al. |
| 9,867,702 B2 | 1/2018 | Keränen et al. |
| 9,877,833 B1 | 1/2018 | Bishop et al. |
| 9,883,941 B2 | 2/2018 | Hastings et al. |
| 9,889,003 B2 * | 2/2018 | Börtlein .............. A61F 2/2409 |
| 9,895,221 B2 | 2/2018 | Vidlund |
| 9,895,222 B2 | 2/2018 | Zeng et al. |
| 9,901,444 B2 | 2/2018 | Valdez et al. |
| 9,918,840 B2 | 3/2018 | Reich et al. |
| D815,744 S | 4/2018 | Ratz et al. |
| 9,949,825 B2 | 4/2018 | Braido et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,647 B2 | 5/2018 | Ganesan et al. |
| 9,974,650 B2 | 5/2018 | Nguyen-Thien-Nhon et al. |
| 9,999,504 B2 | 6/2018 | Czyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,832 B2 | 7/2018 | Quill et al. |
| 10,029,037 B2 | 7/2018 | Muller et al. |
| 10,034,747 B2 | 7/2018 | Harewood |
| 10,034,749 B2 | 7/2018 | Spence et al. |
| 10,039,637 B2 | 8/2018 | Maimon et al. |
| 10,045,846 B2 | 8/2018 | Bonyuet et al. |
| 10,052,198 B2 | 8/2018 | Chau et al. |
| 10,052,199 B2 | 8/2018 | Spence et al. |
| 10,058,318 B2 | 8/2018 | Tegzes |
| 10,058,321 B2 | 8/2018 | Sampson et al. |
| 10,064,719 B2 | 9/2018 | Börtlein et al. |
| 10,070,954 B2 | 9/2018 | Braido et al. |
| 10,092,400 B2 | 10/2018 | Jimenez et al. |
| 10,098,734 B2 | 10/2018 | Hoang |
| 10,105,217 B2 | 10/2018 | Keränen |
| 10,105,224 B2 | 10/2018 | Buchbinder et al. |
| 10,130,464 B2 | 11/2018 | Meiri et al. |
| 10,130,471 B2 | 11/2018 | Keränen et al. |
| 10,143,552 B2 | 12/2018 | Wallace et al. |
| 10,149,759 B2 | 12/2018 | Naor |
| 10,172,708 B2 | 1/2019 | Anderson |
| 10,172,711 B2 | 1/2019 | Keränen |
| 10,179,042 B2 | 1/2019 | Braido et al. |
| 10,195,021 B2 | 2/2019 | Keränen et al. |
| 10,195,025 B2 | 2/2019 | Levi et al. |
| 10,195,027 B2 | 2/2019 | Nasr |
| 10,195,028 B2 | 2/2019 | Hosmer et al. |
| 10,195,029 B2 | 2/2019 | Keränen |
| 10,201,418 B2 | 2/2019 | Biadillah et al. |
| 10,206,775 B2 | 2/2019 | Kovalsky et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,226,339 B2 | 3/2019 | Spence et al. |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,314,701 B2 | 6/2019 | Von Segesser et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,338,724 B2 | 7/2019 | Zhao |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,130 B2 | 7/2019 | Armer et al. |
| 10,363,131 B2 | 7/2019 | Eidenschink et al. |
| 10,368,986 B2 | 8/2019 | Gosal et al. |
| 10,368,990 B2 | 8/2019 | Noe et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,426,608 B2 | 10/2019 | Salahich et al. |
| 10,433,961 B2 | 10/2019 | McLean |
| 10,470,881 B2 | 11/2019 | Noe et al. |
| 10,478,291 B2 | 11/2019 | Nguyen et al. |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |
| 10,524,901 B2 | 1/2020 | Quadri et al. |
| 10,548,729 B2 | 2/2020 | Zipory et al. |
| 10,568,737 B2 | 2/2020 | Noe et al. |
| 10,575,951 B2 | 3/2020 | Johnson et al. |
| 10,603,165 B2 | 3/2020 | Maimon et al. |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,709,552 B2 | 7/2020 | Backus et al. |
| 10,716,662 B2 | 7/2020 | Delaloye et al. |
| 10,722,352 B2 | 7/2020 | Spence |

(56) References Cited

U.S. PATENT DOCUMENTS

| | | |
|---|---|---|
| 10,722,353 B2 | 7/2020 | Levi |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,912,644 B2 | 2/2021 | Argento et al. |
| 10,973,629 B2 | 4/2021 | Levi et al. |
| 10,973,630 B2 | 4/2021 | Torrianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,147,670 B2 * | 10/2021 | Hayoz ............... A61F 2/2466 |
| 11,234,818 B2 * | 2/2022 | Zerkowski ........... A61F 2/2409 |
| 11,547,563 B2 * | 1/2023 | Keränen ............. A61F 2/2466 |
| 11,833,034 B2 * | 12/2023 | Argento ............. A61F 2/2418 |
| 11,877,925 B2 * | 1/2024 | Manash ............. A61F 2/2409 |
| 2002/0173841 A1 | 11/2002 | Ortiz et al. |
| 2003/0114913 A1 | 6/2003 | Spenser et al. |
| 2003/0233142 A1 | 12/2003 | Morales et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137694 A1 | 6/2005 | Haug et al. |
| 2005/0137696 A1 | 6/2005 | Salahieh et al. |
| 2005/0165344 A1 | 7/2005 | Dobak, III |
| 2005/0240202 A1 | 10/2005 | Shennib et al. |
| 2005/0277839 A1 | 12/2005 | Alderman et al. |
| 2006/0009841 A1 | 1/2006 | McGuckin, Jr. et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0195134 A1 * | 8/2006 | Crittenden ........... A61F 2/2445 606/192 |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0027533 A1 * | 2/2007 | Douk ............... A61F 2/2466 623/2.37 |
| 2007/0038292 A1 * | 2/2007 | Danielpour ........... A61F 2/94 623/1.42 |
| 2007/0051377 A1 | 3/2007 | Douk et al. |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0208330 A1 * | 8/2008 | Keranen ............. A61F 2/2448 623/2.36 |
| 2008/0275503 A1 | 11/2008 | Spence et al. |
| 2008/0275540 A1 | 11/2008 | Wer |
| 2009/0088836 A1 * | 4/2009 | Bishop ............. A61F 2/2418 606/192 |
| 2009/0093826 A1 | 4/2009 | Warder-Gabaldon |
| 2009/0138079 A1 | 5/2009 | Tuval et al. |
| 2009/0157174 A1 | 6/2009 | Yoganathan et al. |
| 2009/0192601 A1 | 7/2009 | Rafiee et al. |
| 2009/0209950 A1 | 8/2009 | Starksen |
| 2009/0222026 A1 | 9/2009 | Rothstein et al. |
| 2009/0276040 A1 | 11/2009 | Rowe et al. |
| 2010/0010520 A1 * | 1/2010 | Takahashi ........... A61B 17/064 606/157 |
| 2010/0049239 A1 | 2/2010 | McGuckin, Jr. et al. |
| 2010/0076497 A1 | 3/2010 | Zwirkoski |
| 2010/0076549 A1 | 3/2010 | Keidar et al. |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1 | 12/2010 | Navia et al. |
| 2011/0022164 A1 | 1/2011 | Quinn et al. |
| 2011/0046600 A1 | 2/2011 | Crank |
| 2011/0224785 A1 | 9/2011 | Hacohen |
| 2011/0288637 A1 | 11/2011 | De Marchena |
| 2011/0313515 A1 | 12/2011 | Quadri et al. |
| 2011/0319989 A1 | 12/2011 | Lane et al. |
| 2012/0022633 A1 | 1/2012 | Olson et al. |
| 2012/0053680 A1 | 3/2012 | Bolling et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277734 A1 | 11/2012 | Geotz et al. |
| 2012/0277853 A1 | 11/2012 | Rothstein |
| 2013/0006352 A1 * | 1/2013 | Yaron ............... A61F 2/2427 623/2.37 |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0116779 A1 | 5/2013 | Weber |
| 2013/0123912 A1 | 5/2013 | Tung et al. |
| 2013/0172992 A1 | 7/2013 | Gross et al. |
| 2013/0253643 A1 | 9/2013 | Rolando et al. |
| 2013/0274873 A1 | 10/2013 | Delaloye et al. |
| 2013/0325110 A1 | 12/2013 | Khalil et al. |
| 2014/0005768 A1 | 1/2014 | Thomas et al. |
| 2014/0031928 A1 | 1/2014 | Murphy et al. |
| 2014/0081394 A1 * | 3/2014 | Keranen ............. A61F 2/2445 623/2.38 |
| 2014/0081154 A1 | 5/2014 | Toth |
| 2014/0200649 A1 | 7/2014 | Essinger et al. |
| 2014/0228943 A1 | 8/2014 | Stigall et al. |
| 2014/0249621 A1 | 9/2014 | Eidenschink |
| 2014/0257467 A1 | 9/2014 | Lane et al. |
| 2014/0277382 A1 * | 9/2014 | Dolan ............... A61F 2/915 219/121.72 |
| 2014/0277409 A1 | 9/2014 | Börtlein et al. |
| 2014/0324163 A1 | 10/2014 | Keränen et al. |
| 2015/0005764 A1 | 1/2015 | Hanson et al. |
| 2015/0018876 A1 | 1/2015 | Ewers et al. |
| 2015/0051709 A1 | 2/2015 | Vasquez et al. |
| 2015/0134055 A1 | 5/2015 | Spence et al. |
| 2015/0173897 A1 | 6/2015 | Raanani et al. |
| 2015/0230921 A1 * | 8/2015 | Chau ............... A61F 2/2418 623/2.11 |
| 2015/0250480 A1 | 9/2015 | Featherstone |
| 2015/0265403 A1 | 9/2015 | Keränen |
| 2015/0272737 A1 | 10/2015 | Dale et al. |
| 2015/0297346 A1 | 10/2015 | Duffy et al. |
| 2015/0305863 A1 | 10/2015 | Gray et al. |
| 2015/0328000 A1 | 11/2015 | Ratz et al. |
| 2015/0335290 A1 | 11/2015 | Hunter |
| 2015/0335426 A1 | 11/2015 | Lim et al. |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2015/0374493 A1 * | 12/2015 | Yaron ............... A61F 2/2442 623/2.36 |
| 2016/0074165 A1 * | 3/2016 | Spence ............. A61F 2/2418 623/2.37 |
| 2016/0089126 A1 | 3/2016 | Guo |
| 2016/0095705 A1 * | 4/2016 | Keränen ........... A61F 2/2445 623/2.36 |
| 2016/0113764 A1 | 4/2016 | Sheahan et al. |
| 2016/0143689 A1 | 5/2016 | Ditter |
| 2016/0143731 A1 | 5/2016 | Backus et al. |

(56) References Cited

U.S. PATENT DOCUMENTS

| | | | |
|---|---|---|---|
| 2016/0166380 A1 | 6/2016 | Seguin et al. | |
| 2016/0206853 A1 | 7/2016 | Bolduc et al. | |
| 2016/0228247 A1* | 8/2016 | Maimon | A61F 2/2409 |
| 2016/0235526 A1 | 8/2016 | Lashinski et al. | |
| 2016/0235529 A1 | 8/2016 | Ma et al. | |
| 2016/0324637 A1 | 11/2016 | Hlavka et al. | |
| 2016/0324639 A1 | 11/2016 | Nguyen et al. | |
| 2016/0331523 A1 | 11/2016 | Chau et al. | |
| 2016/0346080 A1* | 12/2016 | Righini | A61F 2/2412 |
| 2017/0007402 A1* | 1/2017 | Zerkowski | A61F 2/2445 |
| 2017/0056163 A1 | 3/2017 | Tayeb et al. | |
| 2017/0071732 A1* | 3/2017 | Conklin | A61F 2/2418 |
| 2017/0079790 A1 | 3/2017 | Vidlund et al. | |
| 2017/0112624 A1 | 4/2017 | Patel | |
| 2017/0119524 A1 | 5/2017 | Salahieh et al. | |
| 2017/0128203 A1 | 5/2017 | Zhang et al. | |
| 2017/0156723 A1 | 6/2017 | Keating et al. | |
| 2017/0165057 A9 | 6/2017 | Morriss et al. | |
| 2017/0189177 A1 | 7/2017 | Schweich et al. | |
| 2017/0216025 A1 | 8/2017 | Nitzan et al. | |
| 2017/0245850 A1 | 8/2017 | Call et al. | |
| 2017/0258585 A1 | 9/2017 | Marquez et al. | |
| 2017/0273788 A1 | 9/2017 | O'Carroll et al. | |
| 2017/0273789 A1 | 9/2017 | Yaron et al. | |
| 2017/0281341 A1 | 10/2017 | Lim et al. | |
| 2017/0311937 A1 | 11/2017 | Bambury et al. | |
| 2017/0348099 A1 | 12/2017 | Mendelson et al. | |
| 2018/0049873 A1 | 2/2018 | Manash et al. | |
| 2018/0055628 A1 | 3/2018 | Patel et al. | |
| 2018/0092763 A1 | 4/2018 | Dagan et al. | |
| 2018/0110622 A1 | 4/2018 | Gregg et al. | |
| 2018/0116790 A1 | 5/2018 | Ratz et al. | |
| 2018/0133003 A1 | 5/2018 | Levi | |
| 2018/0177592 A1 | 6/2018 | Benichou et al. | |
| 2018/0177594 A1* | 6/2018 | Patel | A61F 2/2409 |
| 2018/0206982 A1 | 7/2018 | Haivatov et al. | |
| 2018/0206986 A1 | 7/2018 | Noe et al. | |
| 2018/0206992 A1 | 7/2018 | Brown | |
| 2018/0207395 A1 | 7/2018 | Bulman et al. | |
| 2018/0214267 A1 | 8/2018 | Lally et al. | |
| 2018/0214270 A1 | 8/2018 | Subramanian et al. | |
| 2018/0221014 A1 | 8/2018 | Darabian | |
| 2018/0228608 A1 | 8/2018 | Sheps et al. | |
| 2018/0228610 A1 | 8/2018 | Lashinski et al. | |
| 2018/0235443 A1 | 8/2018 | Smith et al. | |
| 2018/0250126 A1 | 9/2018 | O'Connor et al. | |
| 2018/0250132 A1 | 9/2018 | Ketai et al. | |
| 2018/0263764 A1 | 9/2018 | Manash et al. | |
| 2018/0280171 A1 | 10/2018 | Gloss et al. | |
| 2018/0289473 A1 | 10/2018 | Rajagopal et al. | |
| 2018/0289474 A1 | 10/2018 | Rajagopal et al. | |
| 2018/0289478 A1 | 10/2018 | Quill | |
| 2018/0289480 A1 | 10/2018 | D'ambra et al. | |
| 2018/0289485 A1 | 10/2018 | Rajagopal et al. | |
| 2018/0296335 A1 | 10/2018 | Miyashiro | |
| 2018/0296338 A1 | 10/2018 | Rabito et al. | |
| 2018/0318079 A1 | 11/2018 | Patel et al. | |
| 2018/0325665 A1 | 11/2018 | Gurovich et al. | |
| 2018/0333259 A1 | 11/2018 | Dibie | |
| 2018/0344303 A1 | 12/2018 | Bambury et al. | |
| 2018/0344454 A1 | 12/2018 | Mauch et al. | |
| 2018/0344459 A1 | 12/2018 | Spence et al. | |
| 2018/0344971 A1* | 12/2018 | Suzuki | A61M 25/005 |
| 2018/0360600 A1 | 12/2018 | Zhuang et al. | |
| 2018/0368830 A1 | 12/2018 | O'Carroll et al. | |
| 2019/0000615 A1 | 1/2019 | Tayeb et al. | |
| 2019/0000625 A1 | 1/2019 | O'Carroll et al. | |
| 2019/0008635 A1 | 1/2019 | Francis et al. | |
| 2019/0008639 A1 | 1/2019 | Landon et al. | |
| 2019/0008640 A1 | 1/2019 | Cooper et al. | |
| 2019/0015205 A1 | 1/2019 | Rajagopal et al. | |
| 2019/0021859 A1 | 1/2019 | O'Carrol et al. | |
| 2019/0046315 A1 | 2/2019 | Gao et al. | |
| 2019/0053894 A1 | 2/2019 | Levi et al. | |
| 2019/0053895 A1 | 2/2019 | Levi | |
| 2019/0053898 A1 | 2/2019 | Maimon et al. | |
| 2019/0053899 A1 | 2/2019 | Levi | |
| 2019/0053903 A1 | 2/2019 | Rohl et al. | |
| 2019/0060068 A1 | 2/2019 | Cope et al. | |
| 2019/0060069 A1 | 2/2019 | Maimon et al. | |
| 2019/0060071 A1 | 2/2019 | Lane et al. | |
| 2019/0076244 A1 | 3/2019 | Yohanan et al. | |
| 2019/0076664 A1 | 3/2019 | Ollivier | |
| 2019/0117392 A1 | 4/2019 | Quadri et al. | |
| 2019/0133756 A1 | 5/2019 | Zhang et al. | |
| 2019/0133757 A1 | 5/2019 | Zhang et al. | |
| 2019/0142589 A1 | 5/2019 | Basude | |
| 2019/0159770 A1 | 5/2019 | Rohl et al. | |
| 2019/0160292 A1 | 5/2019 | Peichel et al. | |
| 2019/0167425 A1 | 6/2019 | Reich et al. | |
| 2019/0183649 A1 | 6/2019 | Allen et al. | |
| 2019/0192288 A1 | 6/2019 | Levi et al. | |
| 2019/0192296 A1 | 6/2019 | Schwartz et al. | |
| 2019/0201191 A1 | 7/2019 | McLean et al. | |
| 2019/0209311 A1 | 7/2019 | Zhang et al. | |
| 2019/0209312 A1 | 7/2019 | Zhang et al. | |
| 2019/0209313 A1 | 7/2019 | Zhang et al. | |
| 2019/0209314 A1 | 7/2019 | Zhang et al. | |
| 2019/0209315 A1 | 7/2019 | Zhang et al. | |
| 2019/0209316 A1 | 7/2019 | Zhang et al. | |
| 2019/0209317 A1 | 7/2019 | Zhang et al. | |
| 2019/0209318 A1 | 7/2019 | Zhang et al. | |
| 2019/0209320 A1 | 7/2019 | Draster et al. | |
| 2019/0231520 A1 | 8/2019 | Desrosiers et al. | |
| 2019/0240023 A1 | 8/2019 | Spence et al. | |
| 2019/0246916 A1 | 8/2019 | Kuraguntla et al. | |
| 2019/0254816 A1 | 8/2019 | Anderson et al. | |
| 2019/0261995 A1 | 8/2019 | Goldfarb et al. | |
| 2019/0261996 A1 | 8/2019 | Goldfarb et al. | |
| 2019/0261997 A1 | 8/2019 | Goldfarb et al. | |
| 2019/0262129 A1 | 8/2019 | Cooper et al. | |
| 2019/0282237 A1 | 9/2019 | Goldfarb et al. | |
| 2019/0328518 A1 | 10/2019 | Neumann | |
| 2019/0336282 A1 | 11/2019 | Christianson et al. | |
| 2019/0343625 A1 | 11/2019 | Gharib et al. | |
| 2019/0365530 A1 | 12/2019 | Hoang et al. | |
| 2019/0374337 A1 | 12/2019 | Zamani et al. | |
| 2019/0374342 A1 | 12/2019 | Gregg et al. | |
| 2020/0000579 A1 | 1/2020 | Manash et al. | |
| 2020/0000586 A1 | 1/2020 | Tian et al. | |
| 2020/0008936 A1 | 1/2020 | Cheema et al. | |
| 2020/0022811 A1 | 1/2020 | Griswold et al. | |
| 2020/0054453 A1 | 2/2020 | Zerkowski et al. | |
| 2020/0060813 A1 | 2/2020 | Nguyen et al. | |
| 2020/0060820 A1 | 2/2020 | Ben-Zvi et al. | |
| 2020/0060852 A1 | 2/2020 | Argento et al. | |
| 2020/0078000 A1 | 3/2020 | Rajagopal et al. | |
| 2020/0093601 A1 | 3/2020 | Neustadter | |
| 2020/0107930 A1* | 4/2020 | Argento | A61F 2/2418 |
| 2020/0107932 A1 | 4/2020 | Rabito et al. | |
| 2020/0107933 A1 | 4/2020 | Oba | |
| 2020/0113586 A1 | 4/2020 | Karasic et al. | |
| 2020/0113685 A1 | 4/2020 | Miller et al. | |
| 2020/0113696 A1 | 4/2020 | Ekvall et al. | |
| 2020/0138575 A1 | 5/2020 | Tuval | |
| 2020/0139082 A1 | 5/2020 | Matlock | |
| 2020/0178977 A1 | 6/2020 | Coleman et al. | |
| 2020/0188107 A1 | 6/2020 | Gloss et al. | |
| 2020/0205800 A1 | 7/2020 | Gilmore et al. | |
| 2020/0205969 A1 | 7/2020 | Hacohen | |
| 2020/0205974 A1 | 7/2020 | Zerkowski et al. | |
| 2020/0205975 A1 | 7/2020 | Khairkhahan | |
| 2020/0205979 A1 | 7/2020 | O'Carroll et al. | |
| 2020/0214708 A1 | 7/2020 | Sharma | |
| 2020/0229806 A1 | 7/2020 | Goldfarb et al. | |
| 2020/0229918 A1 | 7/2020 | Pham et al. | |
| 2020/0261220 A1* | 8/2020 | Argento | A61F 2/2418 |
| 2020/0275921 A1 | 9/2020 | Gilmore et al. | |
| 2020/0276017 A1 | 9/2020 | Subramanian et al. | |
| 2020/0297489 A1 | 9/2020 | Bishop et al. | |
| 2020/0297491 A1 | 9/2020 | Argento et al. | |
| 2020/0345492 A1* | 11/2020 | Patel | A61F 2/2436 |
| 2020/0352705 A1 | 11/2020 | Heneghan et al. | |
| 2020/0352706 A1 | 11/2020 | Campbell | |

(56) References Cited

U.S. PATENT DOCUMENTS

| | | |
|---|---|---|
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0154009 A1* | 5/2021 | Argento ............... A61F 2/2427 |
| 2021/0161688 A1 | 6/2021 | Shahriani |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0186689 A1 | 6/2021 | Eidenschink et al. |
| 2021/0228343 A1 | 7/2021 | Scheinblum et al. |
| 2021/0378823 A1 | 12/2021 | Argento et al. |
| 2021/0401572 A1 | 12/2021 | Nasar et al. |
| 2022/0054261 A1 | 2/2022 | Argento et al. |
| 2022/0175522 A1* | 6/2022 | Salahieh ............... A61F 2/2418 |
| 2022/0387755 A1* | 12/2022 | Higgins ............... A61M 60/857 |
| 2022/0401214 A1* | 12/2022 | Saul ....................... A61F 2/2457 |
| 2023/0044256 A1* | 2/2023 | Salahieh ............... A61M 5/007 |
| 2024/0041598 A1* | 2/2024 | Argento ................ A61F 2/2427 |
| 2024/0285396 A1* | 8/2024 | Schwartz ............. A61F 2/2433 |
| 2024/0293217 A1* | 9/2024 | Cartledge ................ A61F 2/04 |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2016 |
| CA | 2954826 C | 10/2019 |
| CN | 103764216 A | 4/2014 |
| CN | 103974670 A | 8/2014 |
| CN | 105358098 A | 2/2016 |
| CN | 107690323 A | 2/2018 |
| CN | 111110401 A | 5/2020 |
| CN | 111110403 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| DE | 102014102650 A1 | 9/2015 |
| EP | 1105181 B1 | 2/2004 |
| EP | 1432369 B1 | 2/2008 |
| EP | 2374415 A1 | 10/2011 |
| EP | 2907479 A1 | 8/2015 |
| EP | 3037064 A1 | 6/2016 |
| EP | 3158975 A1 | 4/2017 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 3244809 B1 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3672528 A1 | 7/2020 |
| EP | 344104581 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | H08131551 A | 5/1996 |
| JP | 2004154177 A | 6/2004 |
| JP | 2008018139 A | 1/2008 |
| JP | 2011506017 A | 3/2011 |
| JP | 2012531270 A | 12/2012 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |
| WO | WO2007/007873 A1 | 1/2007 |
| WO | WO2007/081820 A1 | 7/2007 |
| WO | WO2010/141847 A1 | 12/2010 |
| WO | WO2011/025945 A1 | 3/2011 |
| WO | WO2012/087842 A1 | 6/2012 |
| WO | WO2012/145545 A1 | 10/2012 |
| WO | WO2013/190910 A1 | 12/2013 |
| WO | WO2015/127264 A1 | 8/2015 |
| WO | WO2015/173609 A1 | 11/2015 |
| WO | WO2015/195823 A1 | 12/2015 |
| WO | WO2016/052145 A1 | 4/2016 |
| WO | WO2016/117169 A1 | 7/2016 |
| WO | WO2016/183485 A1 | 11/2016 |
| WO | WO2017/121193 A1 | 7/2017 |
| WO | WO2017/151566 A1 | 9/2017 |
| WO | WO2017/214098 A1 | 12/2017 |
| WO | WO2018/025260 A1 | 2/2018 |
| WO | WO2018/039561 A1 | 3/2018 |
| WO | WO2018/039589 A1 | 3/2018 |
| WO | WO2018/112429 A1 | 6/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO2019/010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/086958 A1 | 5/2019 |
| WO | WO2019/102484 A1 | 5/2019 |
| WO | WO2019/116369 A1 | 6/2019 |
| WO | WO2019/118371 A1 | 6/2019 |
| WO | WO2019/135011 A1 | 7/2019 |
| WO | WO2019/135028 A1 | 7/2019 |
| WO | WO2019/144036 A1 | 7/2019 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/123719 A1 | 6/2020 |
| WO | WO2020/157018 A1 | 8/2020 |
| WO | WO2020/163112 A1 | 8/2020 |
| WO | WO2020/236830 A1 | 11/2020 |
| WO | WO2020/247907 A1 | 12/2020 |
| WO | WO2021/021482 A1 | 2/2021 |
| WO | WO2021/028867 A1 | 2/2021 |
| WO | WO2021/034497 A1 | 2/2021 |
| WO | WO2021/086850 A1 | 5/2021 |
| WO | WO2021/087400 A1 | 5/2021 |
| WO | WO2021/091754 A1 | 5/2021 |
| WO | WO2021/113143 A1 | 6/2021 |
| WO | WO2021/178560 A1 | 9/2021 |
| WO | WO2021/183610 A1 | 9/2021 |
| WO | WO2021/207545 A1 | 10/2021 |
| WO | WO2021/257278 A1 | 12/2021 |
| WO | WO2021/257722 A1 | 12/2021 |
| WO | WO2022/010974 A1 | 1/2022 |
| WO | WO2022/046678 A1 | 3/2022 |
| WO | WO2022/047095 A1 | 3/2022 |
| WO | WO2022/047160 A1 | 3/2022 |
| WO | WO2022/047274 A1 | 3/2022 |

(56) References Cited

FOREIGN PATENT DOCUMENTS

| WO | WO2022/047393 A1 | 3/2022 |
|---|---|---|
| WO | WO2022/047395 A1 | 3/2022 |
| WO | WO2022/066713 A1 | 3/2022 |
| WO | WO2022/066720 A1 | 3/2022 |
| WO | WO2022/174160 A1 | 8/2022 |
| WO | WO2022/271851 A1 | 12/2022 |
| WO | WO2023/034936 A1 | 3/2023 |
| WO | WO2023/049625 A1 | 3/2023 |
| WO | WO2023/064910 A1 | 4/2023 |
| WO | WO2022/204138 A1 | 9/2024 |

OTHER PUBLICATIONS

Schaefer; Large heart valves—small heart valves; ISMAAP; Oct. 19, 2015; 5 pages; retrieved from the internet (https://www.ismaap.org/condition-detail/large-heart-valves-small-heart-valves/) on Mar. 21, 2023.

Argento et al.; U.S. Appl. No. 18/002,219 entitled "Minimal frame prosthetic cardiac valve delivery devices, systems, and methods," filed Dec. 16, 2022.

Adamek-Bowers et al.; U.S. Appl. No. 18/043,458 entitled "Prosthetic valve delivery system," filed Feb. 28, 2023.

Backus et al.; U.S. Appl. No. 18/004,609 entitled "Valve delivery system," filed Jan. 6, 2023.

Mulcahy et al.; U.S. Appl. No. 18/043,480 entitled "Prosthetic cardiac valve delivery devices, systems, and methods," filed Feb. 28, 2023.

Adamek-Bowers et al.; U.S. Appl. No. 18/043,499 entitled "Interface for prosthetic cardiac valve and delivery systems," filed Feb. 28, 2023.

Salahieh et al.; U.S. Appl. No. 18/043,519 entitled "Flared prosthetic cardiac valve delivery devices and systems," filed Feb. 28, 2023.

Scott et al.; U.S. Appl. No. 18/043,526 entitled "Access sheath for prosthetic cardiac valve delivery systems," filed Feb. 28, 2023.

Yang et al.; U.S. Appl. No. 18/043,542 entitled "Anchor for prosthetic cardiac valve devices," filed Feb. 28, 2023.

Argento et al.; U.S. Appl. No. 18/246,307 entitled "Systems, methods, and devices for expandable sensors," filed Mar. 22, 2023.

Argento et al.; U.S. Appl. No. 18/246,311 entitled "Prosthetic cardiac valve sensor devices, systems, and methods with imaging," filed Mar. 22, 2023.

Westaby et al.; Adult human valve dimensions and their surgical significance; The American Journal of Cardiology; 53(4); pp. 552-556; Feb. 1984.

Salahieh et al.; U.S. Appl. No. 17/543,555 entitled "Flared prosthetic cardiac valve delivery devices and systems," filed Dec. 6, 2021.

Yang et al.; U.S. Appl. No. 17/651,040 entitled "Anchor for prosthetic cardiac valve delivery devices and systems", filed Feb. 14, 2022.

Argento et al.; U.S. Appl. No. 17/931,408 entitled "Prosthetic cardiac valve devices, systems, and methods," filed Sep. 12, 2022.

Argento; U.S. Appl. No. 17/906,216 entitled "Prosthetic cardiac valve devices, systems, and methods," filed Sep. 13, 2022.

Argento et al.; U.S. Appl. No. 17/905,556 entitled "Prosthetic cardiac valve devices, systems, and methods," filed Sep. 2, 2022.

Boyd et al.; U.S. Appl. No. 17/995,776 entitled "Valve delivery system", filed Oct. 7, 2022.

Argento et al.; U.S. Appl. No. 18/185,330 entitled "Prosthetic cardiac valve devices, systems, and methods," filed Mar. 16, 2023.

Adamek-Bowers et al.; U.S. Appl. No. 18/255,763 entitled "Mitral valve implants," filed Jun. 2, 2023.

Argento et al.; U.S. Appl. No. 18/494,520 entitled "Prosthetic cardiac valve devices, systems, and methods," filed Oct. 25, 2023.

Mulcahy et al.; U.S. Appl. No. 18/573,816 entitled "Prosthetic cardiac valve delivery devices, systems, and methods," filed Dec. 22, 2023.

Boyd et al.; U.S. Appl. No. 18/688,735 entitled "Guide catheter for prosthetic cardiac valve delivery systems, " filed Mar. 1, 2024.

Adamek-Bowers et al.; U.S. Appl. No. 18/693,856 entitled "Tether delivery of cardiac valve," filed Mar. 20, 2024.

Yang et al.; U.S. Appl. No. 18/700,621 entitled "Cardiac valve prosthesis delivery system and methods of use," filed Apr. 11, 2024.

Masterclass; Knit vs. Woven: Learn How to Identify the Two Fabric Types; Jun. 7, 2021; 13 pages; retrieved from the internet (https://www.masterclass.com/articles/knit-vs-woven-learn-how-to-identify-the-two-fabric-types) on Nov. 15, 2024.

* cited by examiner

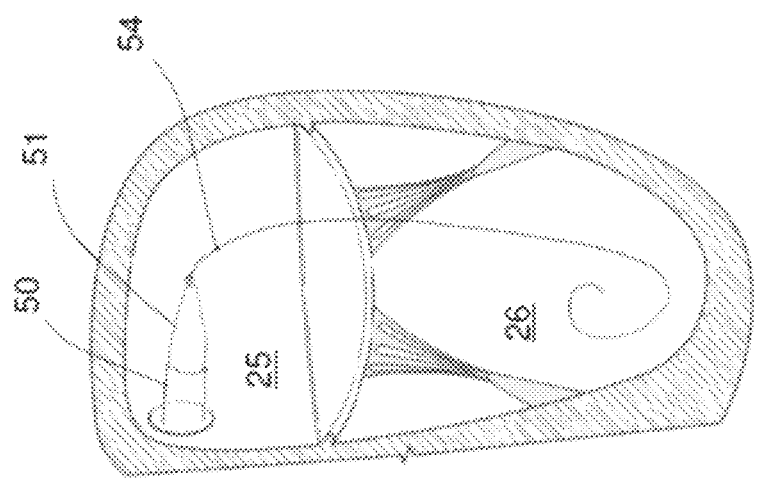
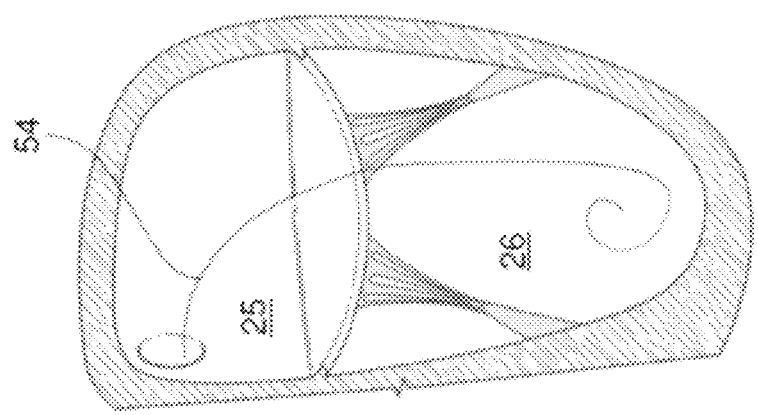

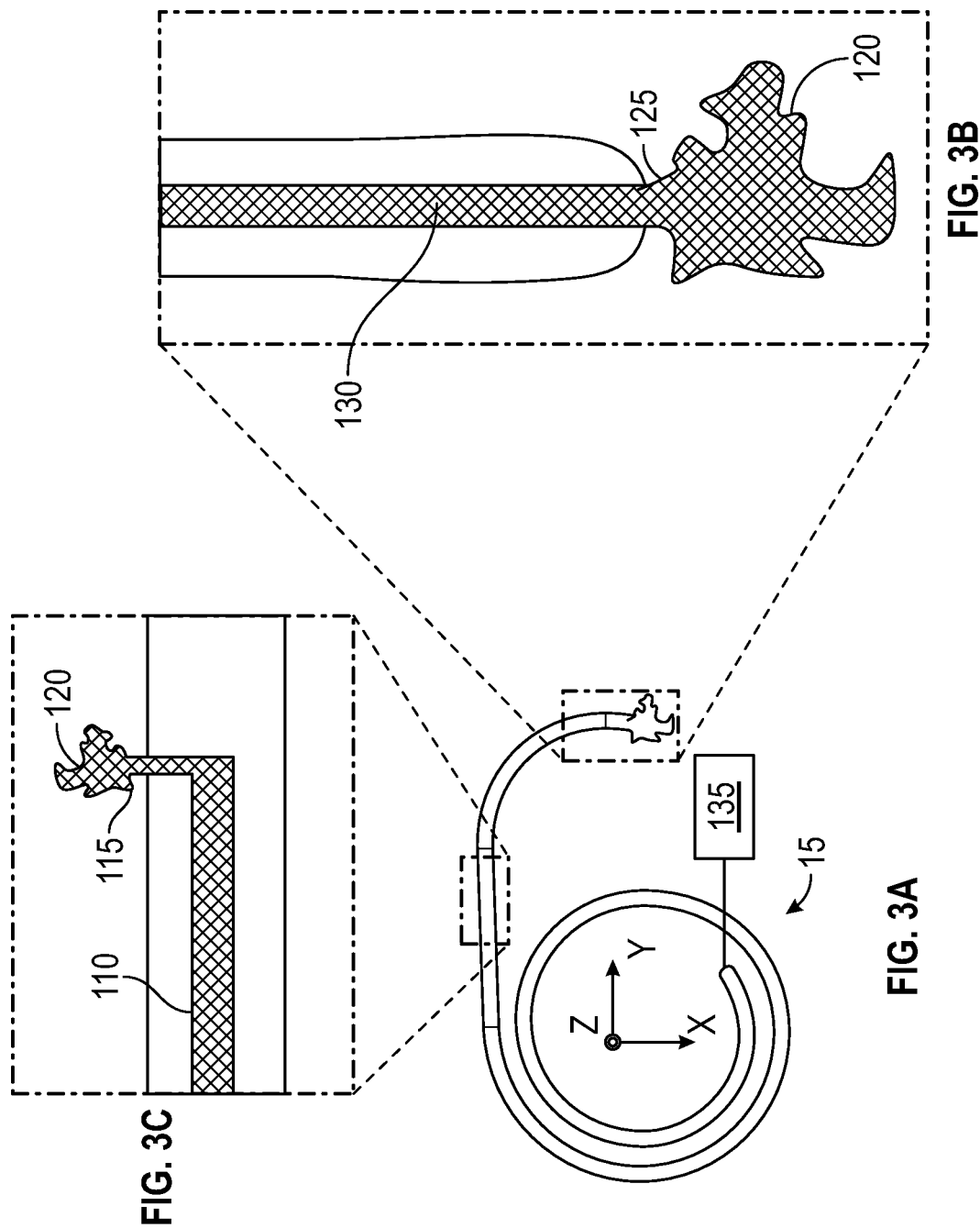

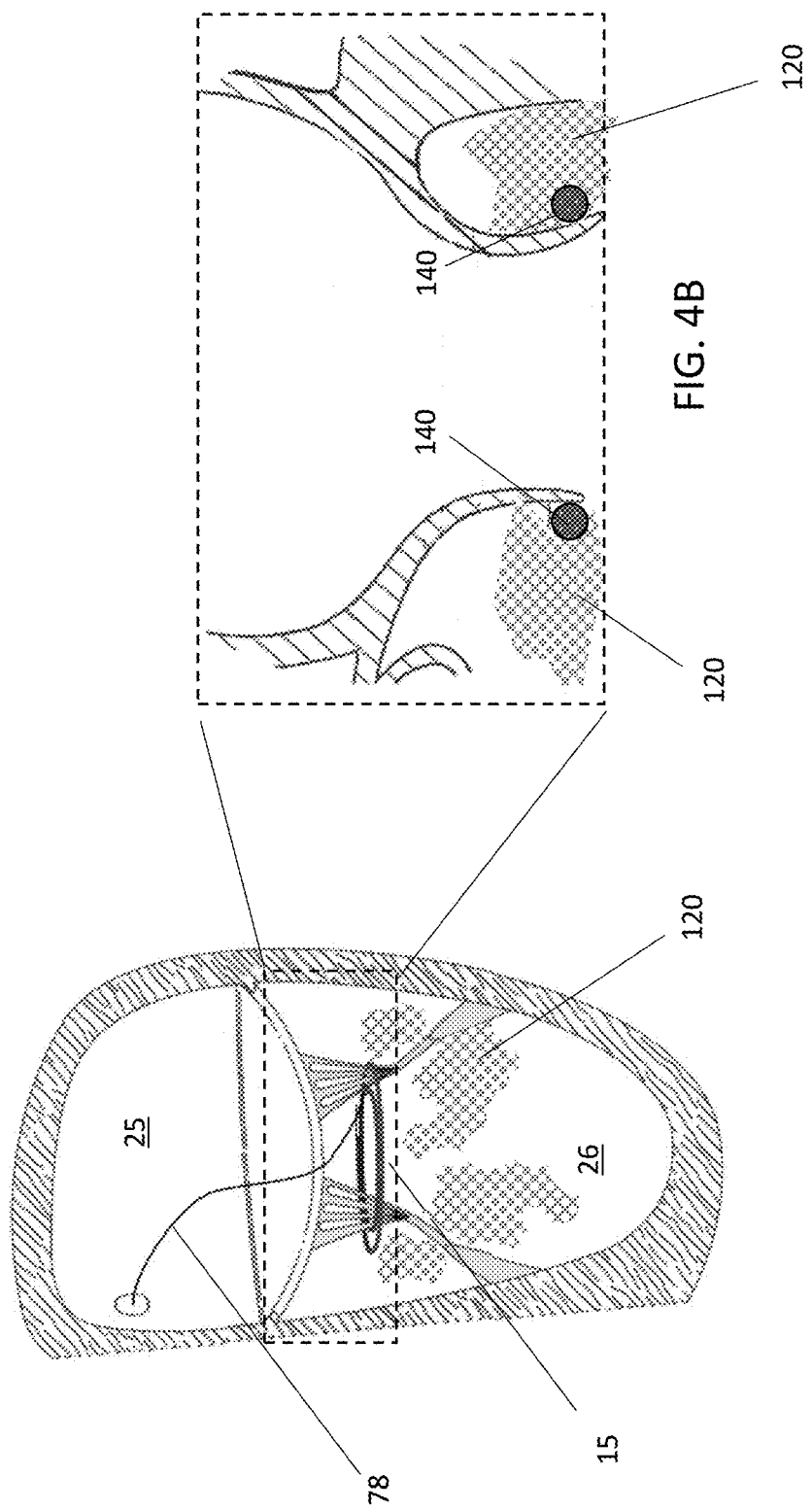

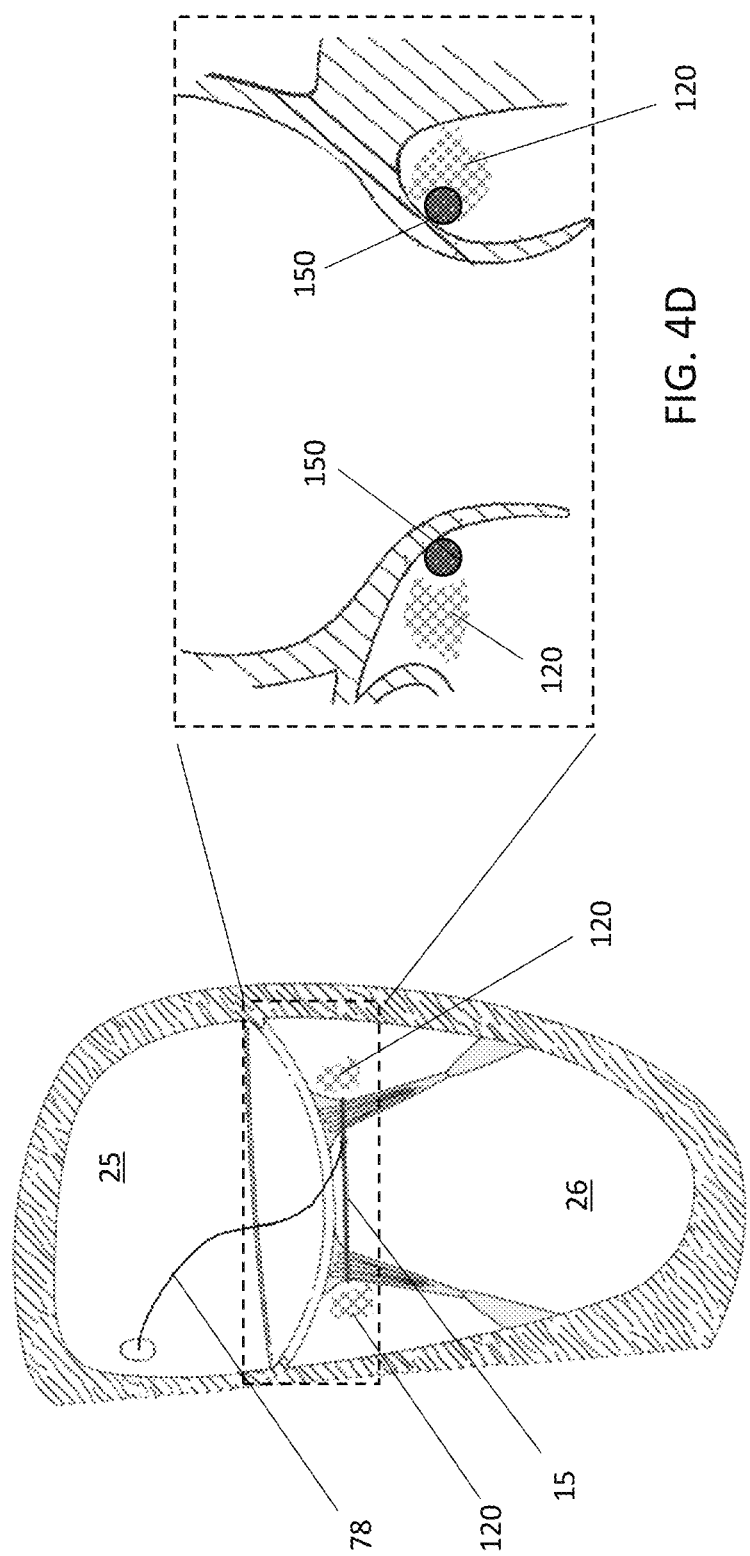

ANCHOR POSITION VERIFICATION FOR PROSTHETIC CARDIAC VALVE DEVICES

CROSS REFERENCE TO RELATED APPLICATIONS

This application claims the benefit of U.S. Provisional Application No. 63/164,514, filed Mar. 22, 2021, which is herein incorporated by reference in its entirety.

BACKGROUND

Blood flow between heart chambers is regulated by native valves—the mitral valve, the aortic valve, the pulmonary valve, and the tricuspid valve. Each of these valves is a passive one-way valve that opens and closes in response to differential pressures. Patients with valvular disease have abnormal anatomy and/or function of at least one valve. For example, a valve may suffer from insufficiency, also referred to as regurgitation, when the valve does not fully close, thereby allowing blood to flow retrograde. Valve stenosis can cause a valve to fail to open properly. Other diseases may also lead to dysfunction of the valves.

The mitral valve, for example, sits between the left atrium and the left ventricle and, when functioning properly, allows blood to flow from the left atrium to the left ventricle while preventing backflow or regurgitation in the reverse direction. Native valve leaflets of a diseased mitral valve, however, do not fully prolapse, causing the patient to experience regurgitation.

While medications may be used to treat diseased native valves, the defective valve often needs to be repaired or replaced at some point during the patient's lifetime. Existing prosthetic valves and surgical repair and/or replacement procedures may have increased risks, limited lifespans, and/or are highly invasive. Some less invasive transcatheter options are available, but most are not ideal. A major limitation of existing transcatheter mitral valve devices, for example, is that the mitral valve devices are too large in diameter to be delivered transseptally, requiring transapical access instead. Furthermore, existing mitral valve replacement devices are not optimized with respect to strength-weight ratio and often take up too much space within the valve chambers, resulting in obstruction of outflow from the ventricle into the aorta and/or thrombosis.

At times, fixation of a valve replacement device to the native anatomy is achieved using an anchor structure that is delivered transcatheter. It can be a challenge for clinicians to confirm that the anchor is properly positioned with respect to the native anatomy during implantation, e.g., due to the size and materials used to construct anchors that are suitable for minimally invasive implantation.

Thus, a new valve device that overcomes some or all of these deficiencies is desired.

SUMMARY OF THE DISCLOSURE

A prosthesis for treating a diseased native valve is provided, the prosthesis comprising a frame structure having a plurality of leaflets therein, and a spiral anchor configured to extend around an outer perimeter of the frame structure, comprising a wall defining a lumen, and at least one port in fluid communication with the lumen, the lumen and the at least one port shaped and sized to transport and deliver a contrast agent that is detectable by a visualization modality.

In additional embodiments, the wall defining the lumen is an interior wall within an outer perimeter of the spiral anchor.

In other embodiments, the wall defining the lumen is continuous from a proximal end to a distal end of the spiral anchor.

In some embodiments, the wall defining the lumen is an exterior wall along an outer perimeter of the spiral anchor (e.g., a monorail).

In some embodiments, a proximal end of the wall is configured to fluidly couple with a distal end of a contrast agent delivery catheter, during the delivery of the prosthesis.

In some embodiments, the at least one port is at a distal tip of the anchor.

In additional embodiments, the at least one port is proximal to a distal tip of the anchor.

In some embodiments, the at least one port is oriented toward a leaflet and/or an annulus of the diseased native valve, when the spiral anchor is near a delivery position with respect to the diseased native valve.

In other embodiments, the delivery position is a sub-annular space of the diseased native valve.

In some embodiments, the contrast agent comprises barium-sulfate, iodine, or an iodine-based material.

A method of delivering a valve prosthesis is provided, comprising advancing a distal end of a delivery device to a first side of a native valve, deploying an anchor from a delivery configuration to a deployed configuration on the first side of the native valve, the anchor comprising at least one port for delivering a contrast agent therefrom, advancing the anchor in the deployed configuration from the first side of the native valve to a second side of the native valve, rotating the anchor in the deployed configuration around one or more structures on the second side of the native valve, delivering the contrast agent through the at least one port, identifying a characteristic of the contrast agent in an image to confirm that the anchor has been rotated around the one or more structures.

In additional embodiments, the method includes releasing the anchor from the distal end of the delivery device.

In some embodiments, delivering the contrast agent comprises delivering into a blood flow path of the heart.

In some embodiments, delivering the contrast agent comprises delivering following the step of advancing to the second side of the native valve.

In other embodiments, the characteristic of the contrast agent comprises an extent of dispersion.

In some embodiments, confirming that the anchor has been fully rotated comprises confirming that dispersion of the contrast agent is substantially confined to a selected region.

In some embodiments, the selected region comprises a sub-annular space of the native valve.

In some embodiments, the method further comprises repeating at least one of the rotating, delivering, and identifying steps until the extent of dispersion is within the selected region.

In other embodiments, the image comprises a fluoroscopic image.

In additional embodiments, the anchor comprises the anchor of claim 1.

BRIEF DESCRIPTION OF THE DRAWINGS

FIGS. 2A-2H show sequential views of an exemplary method of implanting a valve prosthesis.

FIGS. 3A-3C illustrate one embodiment of an anchor that can include one or more structures that are adapted to transport and deliver a contrast agent.

FIGS. 4A-4B illustrate visualization of a contrast agent delivered by an anchor.

DETAILED DESCRIPTION

Described herein are systems, devices, or methods for treatment or replacement of a diseased native valve of the heart, for example a mitral valve.

Figure 1B:
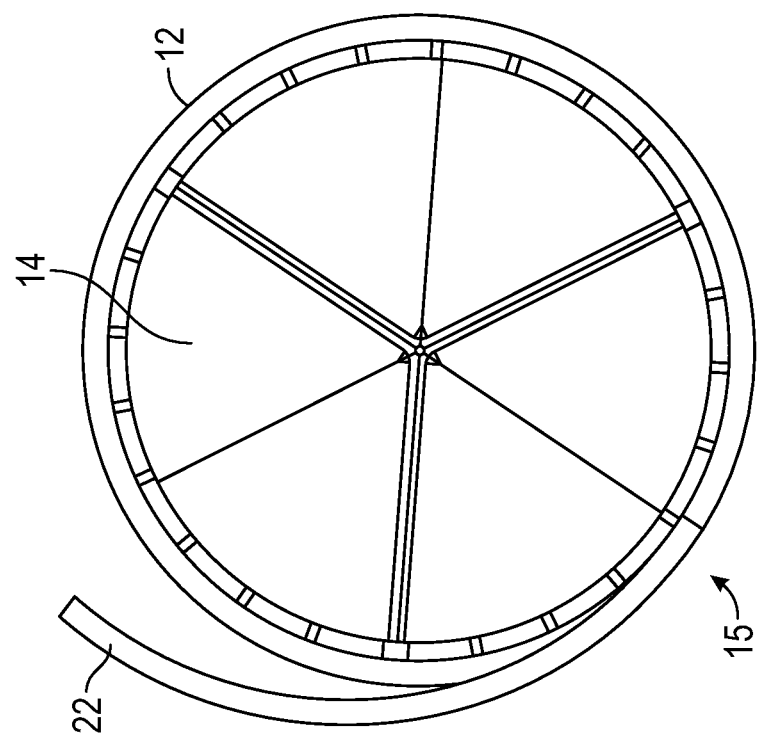
FIGS. 1A-1B show an exemplary valve prosthesis (also referred to herein as "valve device") for replacement of a valve, such as a mitral valve.
Figure 1A:
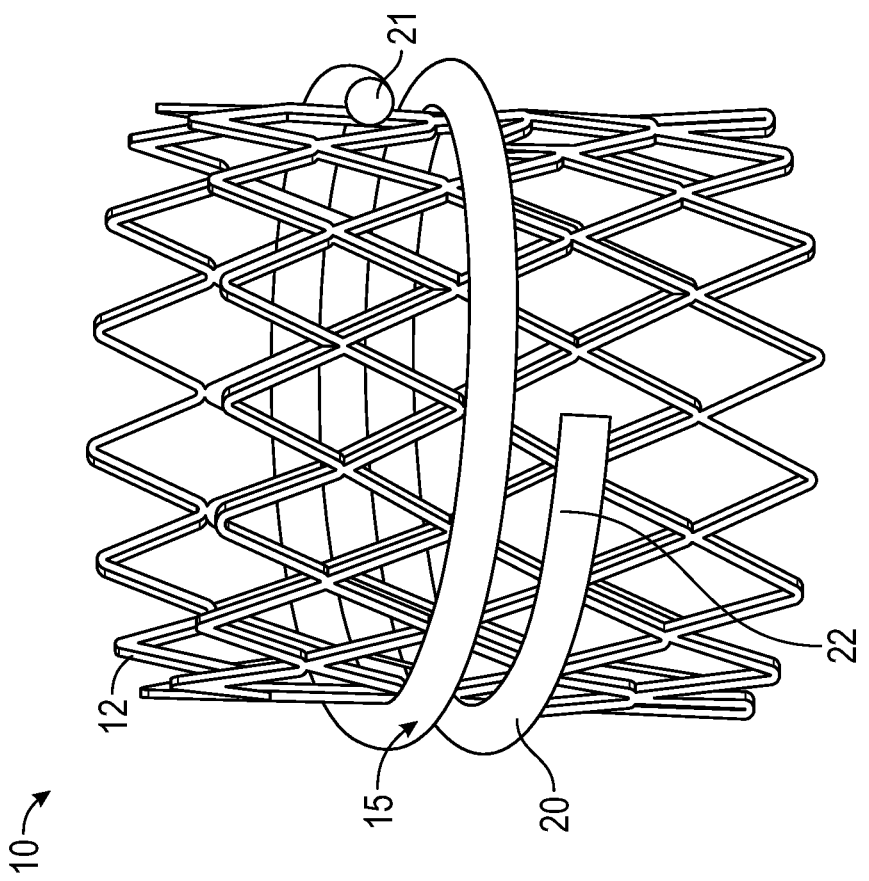

FIGS. 1A-1B show an exemplary valve prosthesis 10 (also referred to herein as "valve device") for replacement of a valve, such as a mitral valve. The illustrated valve prosthesis 10 comprises a frame structure 12, leaflets 14, and an anchor 15. The anchor 15 includes a wire 20 formed in a spiral shape around the frame structure 12.

The exemplary frame structure 12 is configured like a stent. The frame structure 12 has an expanded state and an unexpanded (e.g., collapsed or compressed) state. The compressed state is sized and dimensioned for percutaneous insertion and the expanded state is sized and dimensioned for implantation in a native valve of a patient, such as a mitral valve.

The anchor 15 can include a spiral member, such as wire 20, having a proximal end 21 and a distal end 22. The anchor 15 can be configured to engage with the frame structure 12 via a compression fit. The wire 20 can be formed of a material having sufficient rigidity to hold a predetermined shape. In an exemplary embodiment, the wire 20 can be formed of a shape memory material (e.g. NiTi). Further, the anchor 15 prior to implantation may comprise a flat spiral shape such that loops of the anchor are generally positioned within the same plane (the plane being perpendicular to a longitudinal axis of a delivery device). Additionally, in some embodiments, the distal end 22 can be rounded and/or atraumatic.

The valve prosthesis 10 can be configured for replacing a mitral valve with the distal end 22 configured for insertion through a commissure.

FIGS. 2A-2H show sequential views of an exemplary method of implanting a valve prosthesis 10. At FIG. 2A, a transseptal puncture is made. A guidewire 54 is then routed through the puncture site and left either in the left atrium 25 or across the mitral valve into the left ventricle 26. At FIG. 2B, the outer sheath 50 (optionally with an inner dilator 51) is tracked over the guidewire 54 until the distal end of the outer sheath 50 protrudes into the left atrium 25. The guidewire 54 and inner dilator 51 are then removed from the outer sheath 50. At FIG. 2C, an inner shaft and attached distal anchor guide 153 are inserted through the outer sheath 50 until the distal tip of the anchor guide 153 extends into the left atrium 25. The anchor guide 153 can be positioned and/or oriented as desired by steering the distal end of the sheath 50 and/or rotating the inner shaft and anchor guide 153 relative to the sheath 50. At FIG. 2D, once the anchor guide 153 is in the correct orientation, the anchor 15 can be pushed out through distal tip of the anchor guide 153 (with the distal tip 22 extending out of the guide 153 first). At FIG. 2E, the anchor 15 can fully deploy into the atrium 25. At FIG. 2F, the entire delivery system 30 can be pushed and steered (for example, via steering mechanisms in the outer sheath 50) towards an apex of the ventricle 26, crossing through the mitral valve. In some embodiments, counter-rotation of the anchor 15 may aid in getting the anchor 15 across the mitral valve without tangling. Once the anchor 15 is at the correct depth within the ventricle 26, forward rotation of the anchor 15 (via forward rotation of the inner shaft and guide 153) will allow the anchor 15 to encircle the mitral leaflets and chordae (i.e., with the distal end 22 leading the encircling). At FIG. 2G, the outer sheath 40, inner sheath, and anchor guide 153 are removed, leaving a tether 78 in place (and attached to the proximal end 21 of the anchor 15). Next, the frame structure 12 can then be delivered over the tether 78 and into place within the anchor 15. At FIG. 2H, the frame structure 12 has been delivered, the tether 78 has been released from the proximal end 21 of the anchor 15 to leave the prosthesis 10 in place in the mitral valve 4. As shown in the exemplary FIG. 2H, the anchor 15 is positioned to encircle substantially all of the chordae 42 and is "high" in the ventricle 26. An anchor 15 that has a high position can be adjacent the inferior surface of the annulus of mitral valve 4.

In some embodiments, an anchor 15 is adapted to transport and deliver a biocompatible contrast agent that can enhance an imaging modality image during and/or following delivery of the anchor. The imaging modality can be any modality that is compatible with minimally invasive procedures, such as fluoroscopy and/or echocardiography. Examples of contrast agents (e.g., media) comprise iodine, iodine-based compounds, barium-sulfate, or saline. Without being bound by theory, regarding an x-ray imagining modality, the contrast agent can block or limit the passage of x-rays therethrough. Regarding an ultrasound imaging modality, the contrast agent may possess an increased echogenicity. An anchor 15 that delivers such a contrast agent during and/or following its deployment can alter the appearance of the heart anatomy and/or of the circulation therein, for example of one or more chambers or vessels of the heart.

Referring to FIGS. 3A-3C, in some embodiments, the anchor 15 can include one or more structures that are adapted to transport and deliver a contrast agent 120 from a contrast agent source 135 through the anchor and into or near a target tissue or anatomy of the patient (such as a heart). FIG. 3A depicts an entirety of the anchor 15, including a distal tip (further illustrated in FIG. 3B) and portions of the anchor proximal to the tip (further illustrated in FIG. 3C). It should be noted that in the illustrated embodiment, the distal portion of the anchor 15 can have a larger radius of curvature compared to other, more proximal portions of the anchor, causing the distal portion to extend or "stick out" from the rest of the anchor. It should be understood that other embodiments of the anchor may not have this distal portion that extends outwards, and can instead comprise an anchor that has only a single radius of curvature (such as the anchor depicted in FIG. 1A).

The contrast agent source 135 can be a vessel, container, or volume either disposed within the anchor 15 or remote from the anchor. The contrast agent source 135 is fluidly coupled with the lumen 130 of the anchor. In some embodiments, the contrast agent source can be a syringe exterior to the anchor and to the patient. In other embodiments, the lumen of the anchor can be fluidly coupled to another lumen within a delivery catheter, and the contrast agent source can be either fluidly coupled to the delivery catheter lumen or remote from (but fluidly coupled to) the delivery catheter. The contrast agent source can further include a mechanism for delivering contrast agent from the source into the lumen(s) and out through the port(s) of the anchor. For example, in one embodiment the contrast agent can be delivered by deploying a syringe. In other embodiments, pumps or other ways of pressurizing and/or creating a flow of the contrast agent can be implemented.

As depicted in the example FIG. 3B, in some embodiments, the contrast agent 120 is delivered from a tip of the anchor 15, which comprises a lumen 130 and one or more ports 125. In some embodiments, the lumen 130 is formed by an inner wall of the anchor 15 that is located within an outer perimeter of the anchor (e.g., is substantially centrally located). In some embodiments, the lumen 130 is formed by an outer wall of the anchor 15 (e.g., as a monorail). The lumen 130 can traverse from a proximal portion to a distal portion of the anchor 15. In some embodiments that comprise a monorail construction, the lumen may traverse less than the entirety of the length of the anchor 15. For example, a proximal end of the lumen 130 may terminate distal to a proximal end of the anchor 15, and/or a distal end of the lumen 130 may terminate proximal to a distal end of the anchor 15.

As depicted in the example FIG. 3C, in some embodiments, the contrast agent 120 is delivered from one or more portions of the anchor 15 that are proximal to the tip, where the proximal portions include a lumen 110 and one or more ports 115. In some embodiments, the one or more ports 115 are positioned on the body of the anchor 15 such that, when delivered in a selected orientation and/or position in the heart, the one or more ports 115 are at least partially obstructed by one or more portions of the native heart. For example, an obstruction can comprise a leaflet of the native valve, one or more chordae, an inferior surface of the valve annulus, or a portion of the ventricular heart wall. In some embodiments, the one or more ports 115 are oriented to be generally radially-outward, generally radially-inward, and/or generally along a superior aspect of the anchor 15 (e.g., superior when implanted in the ventricle of the heart).

In some embodiments, feedback regarding an orientation and/or position of the anchor 15 with respect to the native heart anatomy can be provided according to one or more characteristics of the blood flow, visualized in the presence of the contrast agent that is delivered via the anchor 15. Within a ventricle of the heart, blood flow velocity is often reduced in a region that is inferior and peripheral to the valve annulus. In contrast, blood flow velocity within the ventricle is increased within a central region of the chamber, moving toward the apex of the heart. Referring now to FIGS. 4A-4B, in some embodiments an anchor 15 that is position "low" with respect to the sub-annular tissue (e.g., anchor 140 seen in cross-section, FIG. 4B) may release contrast agent 120 into a space having a relatively high blood flow velocity, such that the contrast agent 120 dilutes and/or disperses relatively quickly. The contrast agent 120 may appear to have a reduced or diminished intensity in such a condition, and/or to occupy a greater region of space within the heart. Referring now to FIGS. 4C-D, in some embodiments, an anchor 15 that is positioned in a preferred "high" near the sub-annular tissue (e.g., anchor 150 seen in cross-section, FIG. 4D) may release contrast agent 120 into a space having a relatively low blood flow velocity, such that the contrast agent 120 gathers in the space with little dilution and/or dispersion. The contrast agent 120 may appear to have a greater intensity with the given imaging modality in such a condition. In combination with an appropriate imaging modality, the position of the anchor 15 can be (e.g., indirectly) measured or confirmed by the intensity and/or dispersion of a contrast agent 120.

Figure 2D:
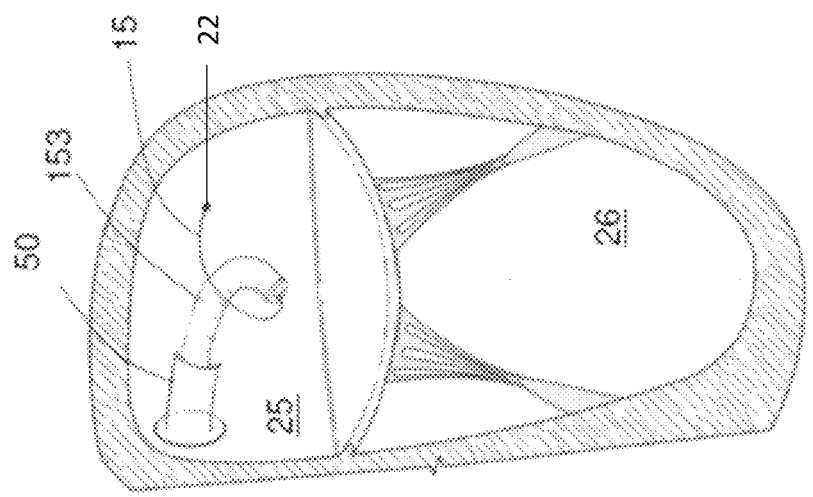
Figure 2C:
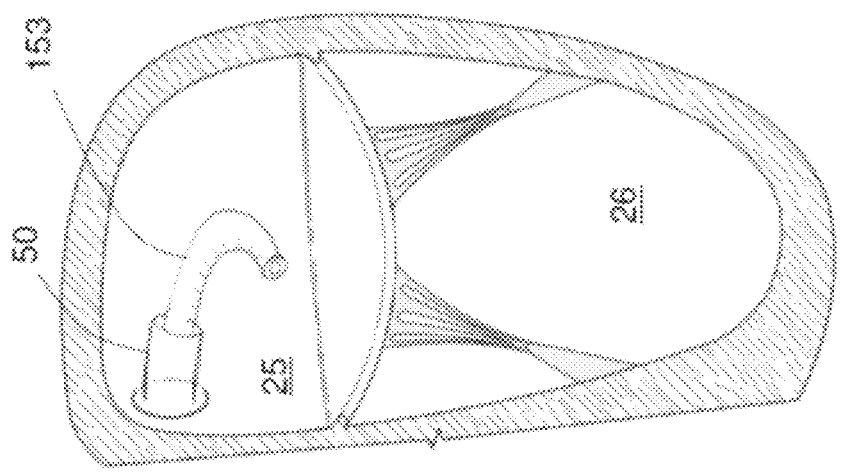
Figure 2F:
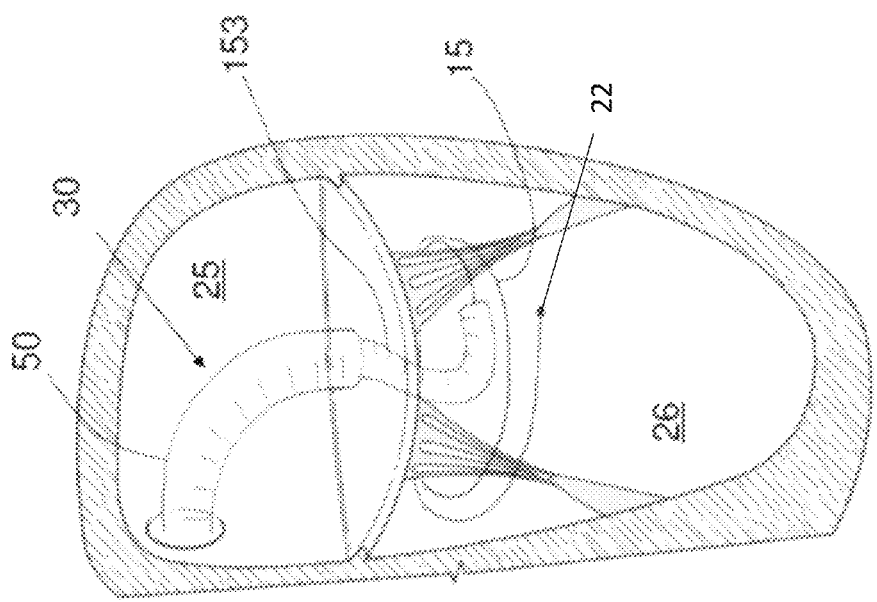
Figure 2E:
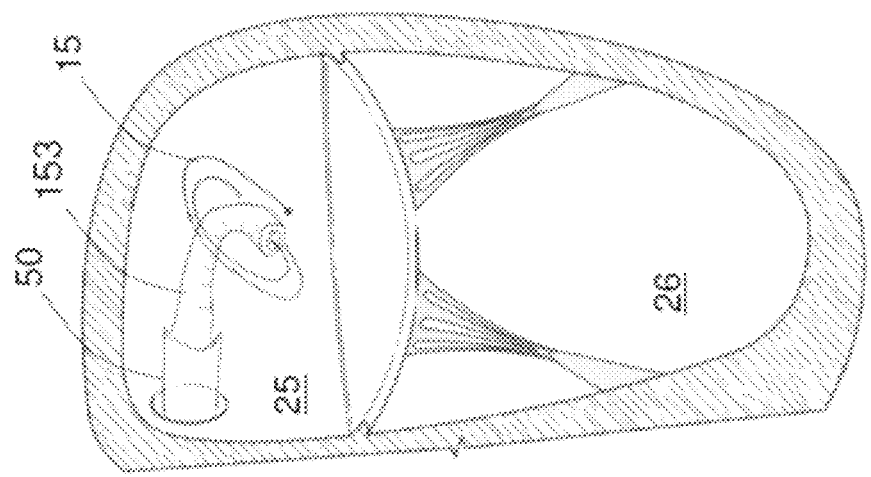
Figure 2G:
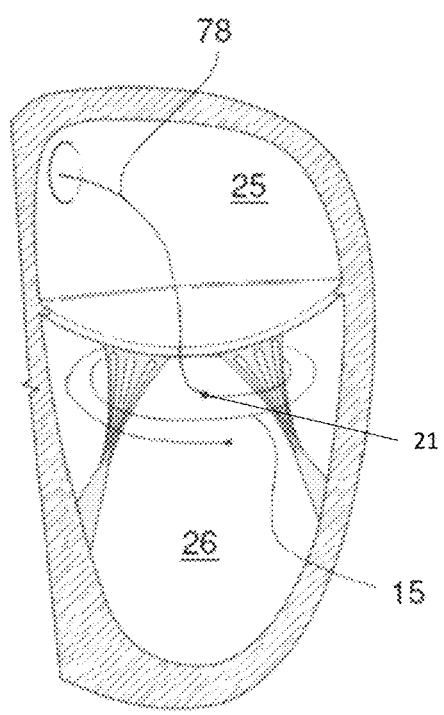
Figure 2H:
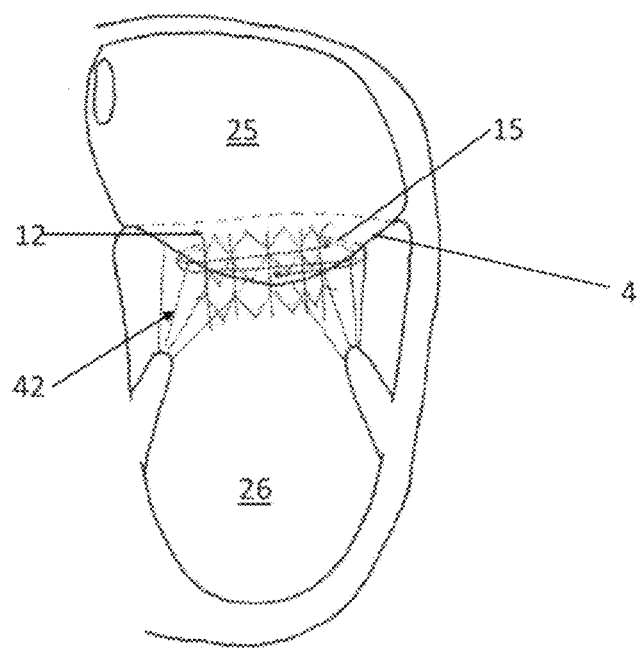
Figure 5:
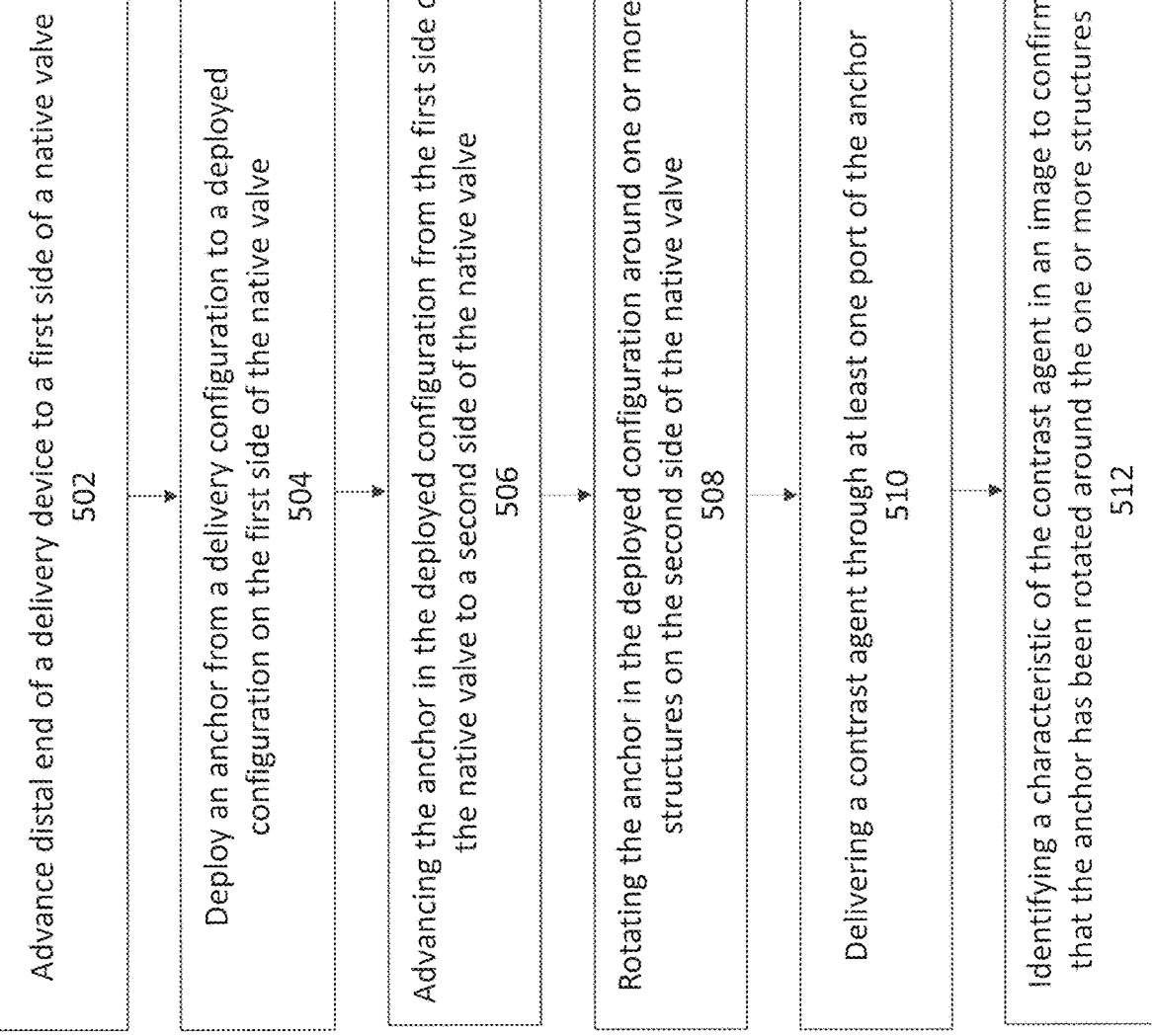
FIG. 5 is a flowchart describing a method of delivering contrast agent with an anchor of a valve replacement device.

FIG. 5 is a flowchart that describes a method of delivering a valve prosthesis including delivering a contrast agent with an anchor of a valve prosthesis. In some embodiments, at step 502, the method can include advancing a distal end of a delivery device to a first side of a native valve (FIG. 2C). At step 504, the method can further include deploying an anchor from a delivery configuration to a deployed configuration on the first side of the native valve (FIG. 2D-FIG. 2E). In some embodiments, the anchor can comprise at least one port for delivering a contrast agent therefrom. At step 506, the method can further include advancing the anchor in the deployed configuration from the first side of the native valve to a second side of the native valve and at step 508, rotating the anchor in the deployed configuration around one or more structures on the second side of the native valve (FIG. 2F). At step 510, the method can include delivering the contrast agent through the at least one port (as shown in FIGS. 3A-3C). Finally, the method can include identifying a characteristic of the contrast agent in an image to confirm that the anchor has been rotated around the one or more structures.

In some embodiments, the method of FIG. 5 can further include releasing the anchor from the distal end of the delivery device.

In some embodiments, delivering the contrast agent comprises delivering into a blood flow path of the heart. In other embodiments, delivering the contrast agent comprises delivering following the step of advancing to the second side of the native valve.

In some examples, the characteristic of the contrast agent comprises an extent of dispersion. In one implementation, confirming that the anchor has been fully rotated comprises confirming that dispersion of the contrast agent is substantially confined to a selected region.

In some examples, the selected region comprises a sub-annular space of the native valve.

In some implementations of the method, the method further includes repeating at least one of the rotating, delivering, and identifying steps until the extent of dispersion is within the selected region.

In some examples, the image comprises a fluoroscopic image.

In other embodiments, the anchor comprises any of the anchors described in this disclosure.

Additional elements of valve prostheses, anchors, and methods of delivery are described in PCT Application No. PCT/US2019/047542 filed on Aug. 21, 2019, PCT Application No. PCT/US2019/057082 filed on Mar. 19, 2019, PCT Application No. PCT/US2019/068088 filed on Dec. 20, 2019, and PCT Application No. PCT/US2020/23671, the entireties of which are incorporated by reference herein in their entireties.

It should be understood that any feature described herein with respect to one embodiment can be substituted for or combined with any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A prosthesis for treating a diseased native valve, the prosthesis comprising:
    a frame structure having a plurality of leaflets therein; and
    a spiral anchor configured to extend around an outer perimeter of the frame structure, comprising
        a wall defining a lumen that is an exterior wall along an outer perimeter of the spiral anchor (e.g., a monorail), and
        at least one port in fluid communication with the lumen, the lumen and the at least one port shaped and sized to transport and deliver a contrast agent that is detectable by a visualization modality.

2. The prosthesis of claim 1, wherein the wall defining the lumen is an interior wall within an outer perimeter of the spiral anchor.

3. The prosthesis of claim 2, wherein the wall defining the lumen is continuous from a proximal end to a distal end of the spiral anchor.

4. The prosthesis of claim 1, wherein a proximal end of the wall is configured to fluidly couple with a distal end of a contrast agent delivery catheter, during the delivery of the prosthesis.

5. The prosthesis of claim 1, wherein the at least one port is at a distal tip of the anchor.

6. The prosthesis of claim 1, wherein the at least one port is proximal to a distal tip of the anchor.

7. The prosthesis of claim 1, wherein the at least one port is oriented toward a leaflet and/or an annulus of the diseased native valve, when the spiral anchor is near a delivery position with respect to the diseased native valve.

8. The prosthesis of claim 7, wherein the delivery position is a sub-annular space of the diseased native valve.

9. The prosthesis of claim 1, wherein the contrast agent comprises barium-sulfate, iodine, or an iodine-based material.

10. A method of delivering a valve prosthesis, comprising:
advancing a distal end of a delivery device to a first side of a native valve;
deploying an anchor from a delivery configuration to a deployed configuration on the first side of the native valve, the anchor comprising at least one port for delivering a contrast agent therefrom;
advancing the anchor in the deployed configuration from the first side of the native valve to a second side of the native valve;
rotating the anchor in the deployed configuration around one or more structures on the second side of the native valve;
delivering the contrast agent through the at least one port into a blood flow path of the heart;
identifying a characteristic of the contrast agent in an image to confirm that the anchor has been rotated around the one or more structures.

11. The method of claim 10, further comprising releasing the anchor from the distal end of the delivery device.

12. The method of claim 10, wherein delivering the contrast agent comprises delivering following the step of advancing to the second side of the native valve.

13. The method of claim 12, wherein confirming that the anchor has been fully rotated comprises confirming that dispersion of the contrast agent is substantially confined to a selected region.

14. The method of claim 11, wherein the characteristic of the contrast agent comprises an extent of dispersion.

15. The method of claim 14, wherein the selected region comprises a sub-annular space of the native valve.

16. The method of claim 14, further comprising repeating at least one of the rotating, delivering, and identifying steps until the extent of dispersion is within the selected region.

17. The method of claim 10, wherein the image comprises a fluoroscopic image.

* * * * *